United States Patent [19]

Thornton

[11] Patent Number: 4,928,675
[45] Date of Patent: May 29, 1990

[54] DENTAL TREATMENT APPARATUS

[76] Inventor: Thomas F. Thornton, 43 Contentment Island Rd., Darien, Conn. 06820

[21] Appl. No.: 274,568

[22] Filed: Nov. 22, 1988

Related U.S. Application Data

[62] Division of Ser. No. 112,278, Oct. 26, 1987, Pat. No. 4,808,109.

[51] Int. Cl.$^5$ .............................................. A61H 9/00
[52] U.S. Cl. .................................. 128/66; 128/62 A; 433/80; 433/112
[58] Field of Search ...................... 433/112, 80, 84, 85; 128/62 A, 66

[56] References Cited

U.S. PATENT DOCUMENTS

| 1,000,785 | 8/1911 | Cunningham et al. | 433/84 |
| 2,469,261 | 5/1949 | Cooper | 433/112 |
| 2,779,100 | 1/1957 | Claessens | 433/80 |
| 3,192,922 | 7/1965 | Winkler | 433/80 |

Primary Examiner—John J. Wilson
Attorney, Agent, or Firm—Dallett Hoopes

[57] ABSTRACT

The process involves the application of heated water, above 40° C., to the teeth with simultaneous rotary brushing to remove plaque. The apparatus is a turbine power unit adapted to be connected to the heated water faucet and adapted to sit in the sink. A heated water exhaust conduit from the unit and a flexible power shaft lead to a handpiece which has a rotary brush driven by the shaft and a nozzle connected to the conduit and directed at the brush.

2 Claims, 3 Drawing Sheets

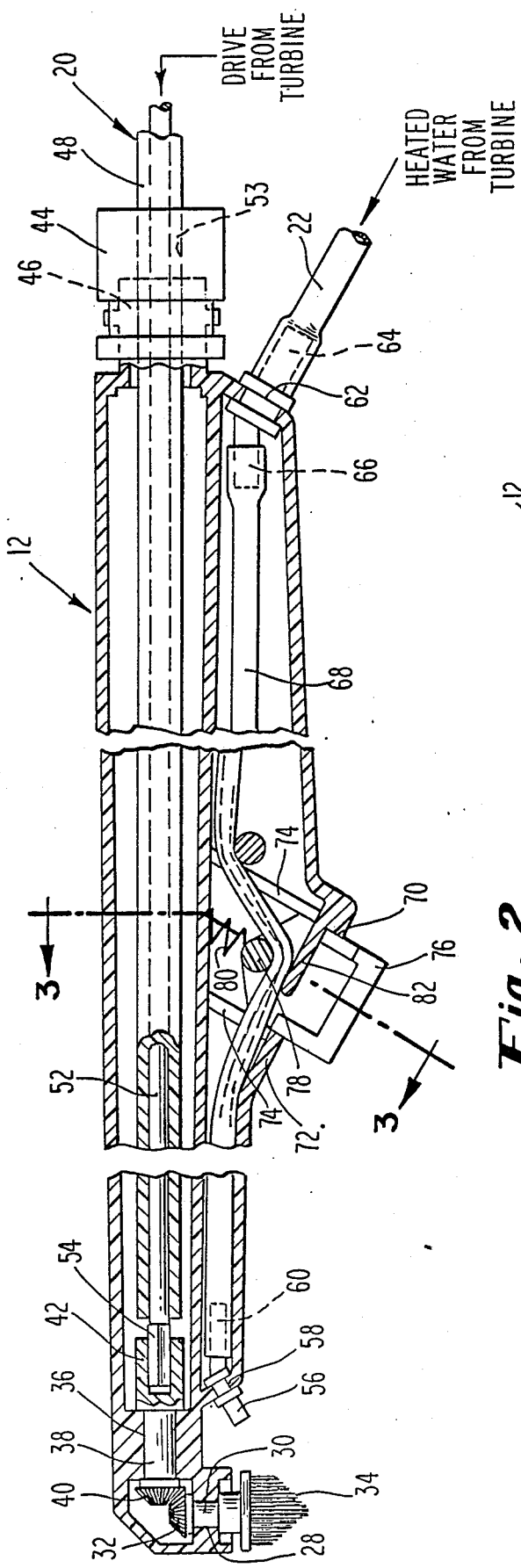
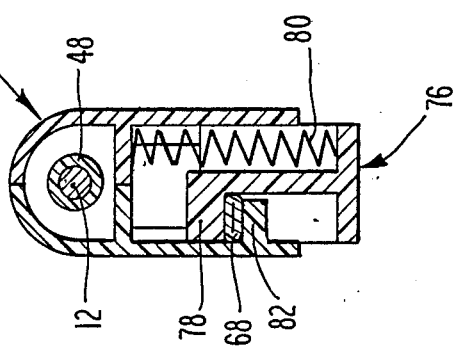
Fig. 2
Fig. 3

DENTAL TREATMENT APPARATUS

CROSS-REFERENCES TO RELATED APPLICATIONS

This application is a divisional application to application Ser. No. 112,278, filed 10/26/87 now U.S. Pat. No. 4,808,109 issued Feb. 28, 1989.

BACKGROUND OF THE INVENTION

1. Field of the Invention

This invention relates to a dental process and apparatus therefor. More specifically, this invention relates to a process for removing plaque from teeth by the application of heated water to the teeth and simultaneous brushing. The invention also relates to an apparatus including a handpiece for directing heated water to the teeth, as well as a rotary brush. A drive unit adapted to be powered by heated water is envisioned, a power shaft from the unit and part of the heated water exhaust being connected to the handpiece.

2. Description of the Related Art Including Information Disclosed Under §§ 1.97–1.99

This invention deals with dental plaque removal. Dental plaque is a colony of bacteria held together by viscid substances called glucans which also help anchor the bacteria to the teeth. Bacteria account for approximately 70 percent of the plaque mass. Glucans account for 20 percent, and levans, which act as energy sources, account for the remaining 10 percent.

When the saliva comes in contact with the bare tooth enamel, a thin amorphous film mainly of glycoproteins rapidly forms on the surface of the tooth. Glycoproteins are molecules with a protein that is combined with carbohydrates. This film is called the acquired pellicle. The acquired pellicle is less than one micron in thickness. The actual bonding of the glycoproteins to the enamel cells is accomplished by means of electrostatic differences between the two. As an example, a protein with a negative charge could adhere to a positive receptor site on the tooth surface, while a molecule with a negative charge would adhere to a site on the tooth surface that had a positive charge. At this initial stage, the acquired pellicle had no colonies of bacteria.

The dental plaque attaches itself to the acquired pellical proteins by interactions similar to the attachment of the proteins to the bare tooth enamel; that is, by means of electrostatic differences between the pellical and the bacterial wall and the glucans. Colonization of the pellical by the bacteria signals the formation of dental plaque. By means of electrostatic charges the bacterial cells adhere to the pellicle, cell walls of other bacteria or glucans making up the intercellular matrix of the plaque.

In the prior art processes for removal of dental plaque have involved the physical scraping of the teeth. Scraping coupled with ultrasonics and water spray has also been used.

Apparatus for treating the teeth in the past have taken various forms. Generally pertinent to the apparatus of the invention are various water-driven devices for brushing the teeth. Examples are disclosed in patent No. 2,283,314, which issued May 19, 1942 to J. L. Ckola. Such devices have included water-driven turbines, located directly in or on the handpiece, and a brush at the opposite end of the handpiece. In some cases, water from the turbine has been delivered to the brush. Other examples are patent No. 3,909,867, which issued Oct. 7, 1975 to Hogsell; No. 4,257,433, which issued Mar. 24, 1981 to Kwan; No. 4,336,622, which issued June 29, 1982 to Teague, Jr. et al.

SUMMARY OF THE INVENTION

The process of the invention is the application of heated water to the teeth with simultaneous brushing. Temperatures of above 40° C. are contemplated, the range of 40° C. to 50° C. being preferred.

The dental plaque is a product of millions of yarns of evolution at 98.6° F. (37° C.). I have discovered the plaque matrix is severely traumatized and weakened with the application of heated water substantially above 98.6° F. I have also discovered that the application of heated water to the binding sites of the acquired pellicle and the tooth enamel as well as the binding sites of the plaque to the pellicle weakens the binding attraction by means of the heat increasing the vibration of the molecules. This increase in vibration and the decrease in binding properties results in more efficient cleansing of plaque and pellicle alike when the application of heated water is accompanied by simultaneous brushing. The physical chemistry phenomenon of heated water on binding sites is clear. However, the biological effects of heated water on plaque is not exactly known. The heated water breakdown of the dental plaque matrix is a function of severe environmental alteration of temperature.

The device described herein provides simultaneous brushing and application of heated water to the site to be cleaned. By means of physical chemistry phenomenon associated with the observed effect of heated water of approximately the 40° C. to 50° C. range, the plaque and pellicle have a tendency to slide from their binding sites more readily and therefore brushing is made inherently more efficacious.

It is especially important to brush simultaneously with the bath of heated water, because plaque colonies have an inherent protective mechanism that has evolved whereby heated liquids and foods cannot destroy plaque colonies due to the protective insulative effects of multiple layers of bacterial cells. The plaque colonies must be dispersed and disturbed by brushing simultaneously with heated water rinsing in order for the invention to work properly.

Aside from the removal of plaque the process of the invention dilutes out sugars in the mouth because of the heavy rinsing with water. Another benefit of the heated water bath is the engorgement of the gingiva with blood upon the application of heat. This general engorgement of tissues when heat is applied is especially important, because the gingiva fluid flow rate is increased as the gingiva presses against the tooth surface. The increase exudate is brushed away simultaneously.

The apparatus of the invention is a handpiece providing a rotary brush and a nozzle directed toward the brush. Spaced from the handpiece and adapted to be positioned in the bathroom sink is a rotary water-driven power unit. Means are provided to deliver heated water from the faucet to the unit to drive an impeller thereinside, and a flexible drive shaft and heated water conduit connects the power unit and the handpiece.

Other objects and features of the invention will be apparent from the following specification including drawings, all of which disclose a non-limiting form of the invention.

BRIEF DESCRIPTION OF THE DRAWINGS

In the drawings:

FIG. 2 is an enlarged sectional view taken on the line 2—2 of FIG. 1 of a handpiece embodying the invention;

FIG. 3 is a sectional view taken on the line 3—3 of FIG. 2;

DESCRIPTION OF THE PREFERRED EMBODIMENT

Figure 1:
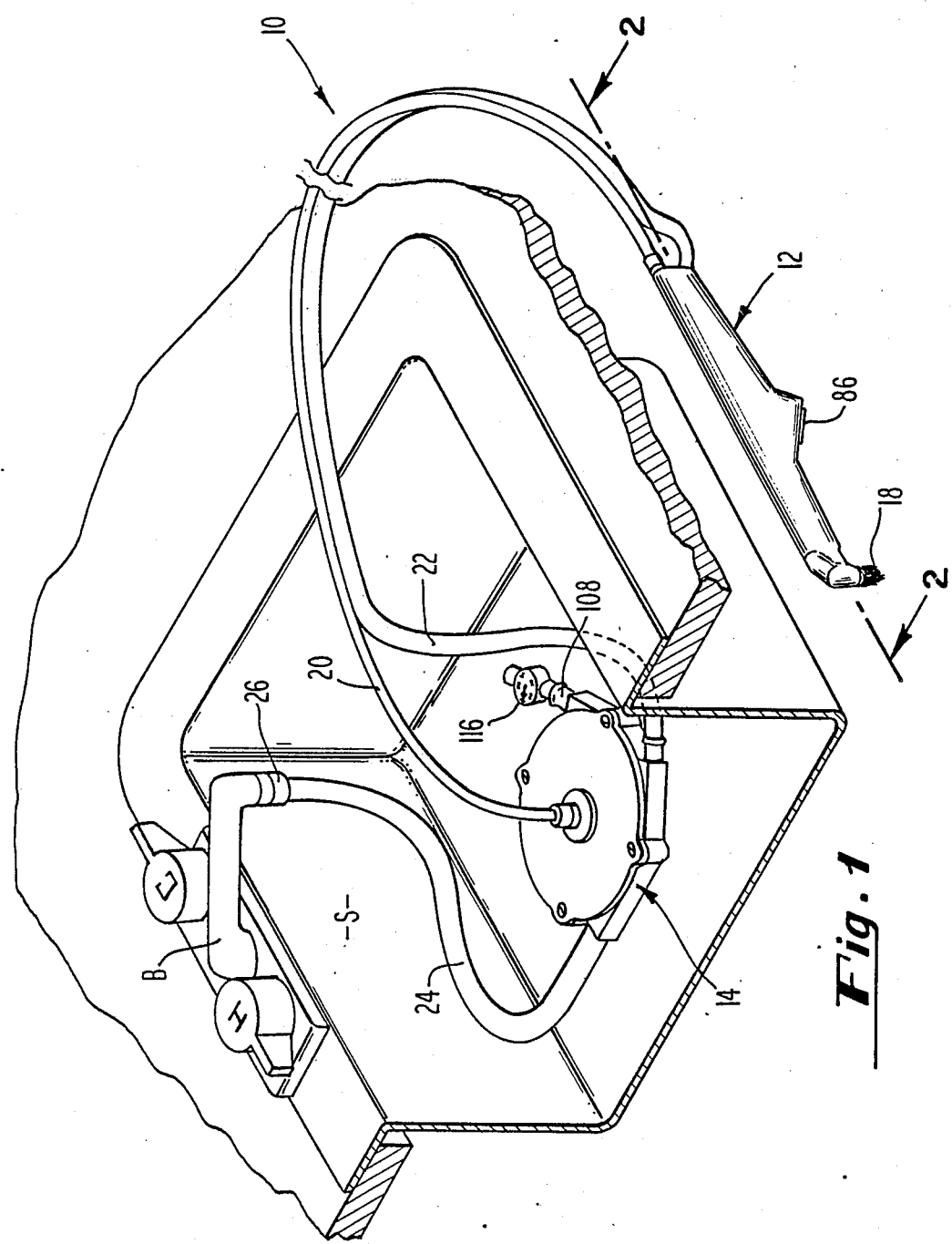
FIG. 1 is a perspective view of an apparatus embodying the invention in which the drive unit is disposed in a sink and the handpiece is therealongside. Portions of the sink and counter are broken away to make the drawing more clear.

An apparatus embodying the invention is shown in FIG. 1 and generally designated 10. It comprises a handpiece 12 and a power-drive unit or turbine 14. In use, the power unit is positioned on the bottom wall of a sink S, whereas the handpiece 12 may be freely manipulated so that its brush 18 can be brought in contact with the teeth.

A flexible drive shaft 20 and a flexible conduit tube 22 connect the power unit and the handpiece. Supply water is delivered to the power unit through a tube 24 coupled to the blender B between the hot and cold water controls H and C, preferably by snap-on coupling means 26, not a part of the invention.

As shown in FIG. 2, the handpiece comprises a hollow housing formed from a pair of molded halves generally having identical but opposite shapes (FIG. 3).

Molded into one end of the housing is a journal 28 for a brush shaft 30. As shown, the upper end of the brush shaft 30 carries a bevel gear 32 and the lower end is fitted with a removable, generally cone-shape bristle brush 34. The bristle brush is pressed on to the bottom of the shaft 30 and may be readily removed for replacement.

At right angles to journal 28 is journal 36, mounting for rotation an intermediate shaft 38, the forward end of which is formed with a bevel gear 40 meshing with gear 32.

The rearward end of shaft 38 is formed with a coupling 42 presenting a rewardly facing opening having preferably a square cross sectional contour.

At the rear end of the handpiece a B.N.C. coupling 44 is connected to a female element 46 having diametrically opposed outward lugs molded about the rear end of the handpiece. Coupled to the opposite side of the ferrule in swivel fashion is the nylon casing 48 of the flexible drive. As shown, the casing snugly surrounds the drive wire 52, still permitting it to turn.

In the rear end of the handpiece, a third journal 53 mounts for rotation the drive wire 52 of the flexible shaft. The forward end of the wire is formed with a square male coupling element 54 which is recessed into the opening in the coupling 42 so that rotation of the wire 52 will drive the brush, through the pair of bevel gears as shown.

A nozzle 56 is mounted in an opening 58 on the underside of the handpiece adjacent the brush 34, and is directed toward the center of the brush. The nozzle element extends rearwardly inside the handpiece in the form of a nipple 60.

At the opposite end of the handpiece on the underside is a fitting 62 which includes a rearward spud 64 and an inward nipple 66. A plastic tube 68 extends between the two nipples 60 and 62 and has its ends telescoped thereover. As a result, the flexible conduit 22 is connected through the tube 68 to the nozzle 56 which directs water toward the center of the brush.

An opening 70 is formed on an inclined wall 72 in the bottom of the housing 12 of the handpiece. Arcuate guides 74 extend upward at an angle from the opening 70 and house a button 76, which has a cross bar 78 disposed across its inner end. A spring 80 urges the button outward so that the cross bar 78 pinches the tube 68 against a stationary stop 82 to close off the water supply therethrough. Thus, flow of water through the tube 68 and out the nozzle 56 may be controlled by pressing or releasing the button 76.

Figures 4, 5:
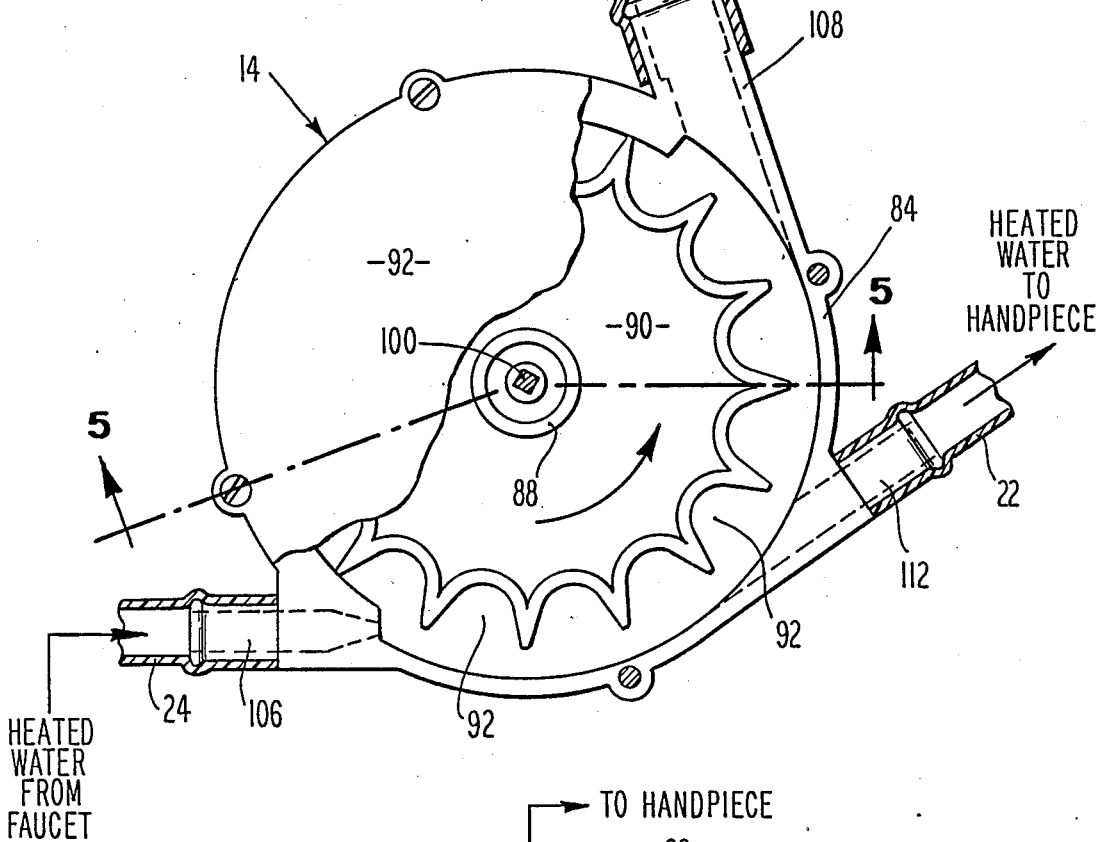
FIG. 4 is an enlarged view of a power unit embodying the invention with the cover partly broken away to reveal the internal impeller.
FIG. 5 is a sectional view taken on the line 5—5 of FIG. 4.

The drive unit 14 is disclosed in FIG. 4. It comprises a shallow cup 84 having a central recess 86 (FIG. 5) which receives the hub 88 of an impeller 90. Preferably, as shown, the impeller is of the bucket-type having buckets 90a, and it is shaped more or less like a bicycle sprocket, but having substantial width. With the cover 92 bolted in place on the cup 84 the upper end of the hub 88 fits into the recess 94.

In its center the impeller is formed with a coupling 96 similar to coupling 42 in the handpiece and presenting a square opening 98 receiving the square driving end 100 of the wire 52 of the flexible drive 20. A second swivelling B.N.C. coupling 102 secures the end of the nylon casing 48 of the flexible drive to the molded female tubular end 104 of the cover 92. End 104 has outward lugs as with element 46.

A tapered inlet 106 directs the incoming water through tube 24 tangentially into the power unit. On the opposite side of the unit is a tangential outlet 108 which permits the spent water to drain into the sink. The housing of the power unit is designed so that a space 110 is provided between the extremities of the impeller 90 and the inside of the wall of the cup 84. This permits the continuous flow of water through the unit and makes the stalling of the impeller much less likely than it would be were the parts relatively close fitting.

Intermediate the inlet 106 and outlet 108 is a tangential tap 112. This connects to the flexible hose 22 and supplies hot water eventually to the nozzle 56 of the handpiece.

A proper balance must be achieved between the size of the openings in the tangential inlet 106, the tap 112 and outlet 108, so that the passage in outlet 108 will not be so small to create back pressure which would limit the power of the impeller 90, but yet narrow enough to assure proper flow through the tap 112 to provide ample water to the nozzle 56.

Rubber feet 114 may be provided on the unit to make the unit more stable in the event the sink has sloping walls. The feet 114 also reduce vibration.

A pass-through analog thermometer 116 is provided. Illustratively it is shown on the exhaust 108. It may be mounted anywhere along the flow of water, preferably on the outlet side of the power unit.

The materials of which the drive unit parts are made must be selected in a way that will avoid any impairment of the operation due to the expansion of parts. Preferably the impeller and its housing are all of the same material, a plastic such as Celcon, a product of the Celanese Corporation, being a preferred choice.

From the above, the use of the apparatus should be clear. The faucet F is turned on to deliver heated water at a temperature at above 40° C. and preferably in the range 40° C. to 50° C., to the power unit 14 through hose 24. This will cause the impeller 90 and brush 18 to rotate along with wire 52. Water travels from tap 112 through the flexible conduit 22 to the handpiece. When the brush 18 is subsequently applied to the teeth, button 86 may be depressed, causing heated water to discharge out nozzle 56. By the handpiece the brush 18 along with the heated water from nozzle 56 may be manipulated along the teeth, causing the aforesaid removal of placque.

While the invention has been described and illustrated showing a single embodiment of apparatus, the invention is not so limited but may be defined by the following claim language including appropriate equivalents thereof.

I claim:

1. An apparatus for treating the teeth comprising a hollow cylindrical housing having a turbine journaled for rotation therein, the turbine having a central spindle, a water supply hose connected to an inlet tangential to the periphery of the housing and having a distal end with means to connect it to a sink water faucet, flexible drive means having one end connected to the spindle to rotate therewith, a handpiece including an elongated body receiving the distal end of the flexible drive and including rotary brush means and means connecting the distal end of the flexible drive means to the rotary brush to rotate it, exhaust passage means for the housing disposed on the periphery of the housing at a point spaced therearound from the inlet, rinse tap means in the housing disposed on the circumference thereof between the inlet and the outlet, nozzle means on the handpiece adjacent the brush and aimed at the brush and flexible conduit means connected between the tap and the nozzle, valve means in the handpiece adapted normally to close off the conduit means but openable to permit flow of water from the housing to the nozzle and a water-temperature-reading thermometer disposed in the exhaust passage means.

2. An apparatus for removing plaque from dental surfaces by simultaneous brushing and treating with hot water at least 40° C. comprising:
   (a) means for supplying hot water,
   (b) toothbrush means having an elongate handle and a brush,
   (c) a flexible hose connecting the means for supplying hot water to the toothbrush means and extending along the handle to the brush to dispense hot water adjacent the brush, and
   (d) a hot-water-temperature-reading thermometer mounted on the apparatus and exposed to the hot water to measure the temperature of the water delivered to the brush.

* * * * *